United States Patent [19]

Tiitto et al.

[11] Patent Number: 4,599,563
[45] Date of Patent: Jul. 8, 1986

[54] BARKHAUSEN NOISE METHOD FOR ANALYZING THE ANISOTROPIC PROPERTIES OF FERROMAGNETIC STEEL

[75] Inventors: Seppo I. Tiitto; Kirsti I. Mielityinen-Tiitto, both of Pittsburgh, Pa.

[73] Assignee: American Stress Technologies, Inc., Pittsburgh, Pa.

[21] Appl. No.: 538,968

[22] Filed: Oct. 4, 1983

[51] Int. Cl.[4] .................. G01R 33/12; G01N 27/72; G01B 7/24
[52] U.S. Cl. .................... 324/232; 73/779; 324/209; 324/243
[58] Field of Search ............... 324/209, 228, 232, 239, 324/240, 242, 243; 73/587, 779, 801

[56] References Cited

U.S. PATENT DOCUMENTS

2,031,469  2/1936  Drake .................. 324/217
3,427,872  2/1969  Leep et al. ............ 73/779

FOREIGN PATENT DOCUMENTS

728071  4/1980  U.S.S.R. .............. 324/209
842654  6/1981  U.S.S.R. .............. 324/209

OTHER PUBLICATIONS

Sundstrom et al; The Use of Barkhausen Noise Analysis in Nondestructive Testing, *Materials Evaluation*, Feb. 1979, pp. 51-56.

Primary Examiner—Gerard R. Strecker
Attorney, Agent, or Firm—Robert D. Yeager; Christine R. Ethridge

[57] ABSTRACT

A method for analyzing the anisotropic properties of ferromagnetic steels by use of Barkhausen noise simultaneously sensed in a plurality of directions without contact with the steel specimen.

3 Claims, 6 Drawing Figures

Fig. 2.

| Texture | Type | r | Sheet Quality | Noise Pattern |
|---|---|---|---|---|
| {001} <100> | CF1 | 1 | Intermediate |  |
| {001} <1̄10> | CF2 | ~0 | Poor |  |
| {011} <100> | CE1 | ≲1 | Intermediate |  |
| {011} <01̄1> | CE2 | ∞ | Very Good |  |
| {111} <01̄1> | CC1 | ≥1 | Good |  |
| {111} <112> | CC2 | ≥1 | Good |  |

Fig. 4.

| Noise Pattern | Group | Sheet Quality |
|---|---|---|
|  | I & II | Good |
|  | III & IV | Intermediate |
|  | V | Poor |

BARKHAUSEN NOISE METHOD FOR ANALYZING THE ANISOTROPIC PROPERTIES OF FERROMAGNETIC STEEL

BACKGROUND OF THE INVENTION

1. Field of the Invention

This invention relates to a method for analyzing the anisotropic properties of ferromagnetic steels; more particularly, to a method which measures the anisotropic properties of such steels by use of Barkhausen noise simultaneously sensed in a plurality of directions without contact with the steel being analyzed.

2. Description of the Prior Art

In the processing of steel, it has long been the desire of workers in the art to analyze the properties, both chemical and physical, of the steel at an early stage in its formation to determine whether the steel will be suitable for its intended purpose. Chemical analysis has been advanced by a number of process improvements including more careful selection of charging materials, off-gas analysis in the basic oxygen furnace and the like. The measurement of physical properties, however, has continued to be essentially a sampling procedure where, for example, a piece of strip steel is removed from a coil after cold-rolling and tested for the physical properties of interest. This "off-line" testing suffers at least two drawbacks: First, the properties of the test piece may not be representative of the entire coil, i.e., the testing is random. Second, little opportunity is afforded for making "upstream" corrections, for example in a cold-rolling operation, to cure defects resulting from process conditions being applied there.

Accordingly, a need exists for an accurate technique for "real-time" testing of the physical properties of steel, i.e., as it is being processed, as well as better assurance that test results are representative of the physical properties of an entire sheet or coil of steel. The former would reduce the amount of in-plant scrap generation; the latter, of course, would dramatically reduce the instances of customer rejection of products because of the inexactness of random sampling methods now employed.

The type of testing under consideration here is called nondestructive testing (NDT). Well-known NDT methods are, for instance, eddy current and ultrasonic analysis, and possibly X-ray diffraction. The eddy current method has been successfully used for fast inspection of surface cracks and material characteristics. Ultrasonic methods work well for internal crack and void detection, and attempts have been made to employ ultrasonic methods for stress measurement. X-ray diffraction is considered to be too slow and complicated for on-line inspection. Another method of nondestructive testing of ferromagnetic steels involves the use of Barkhausen noise or the Barkhausen effect. An excellent review of this subject appears in a paper entitled "The Barkhausen Effect And Its Application To Nondestructive Evaluation" published in October 1979 by the Nondestructive Testing Information Analysis Center, Southwest Research Institute, San Antonio, Tex. As that article points out, when a magnetic field of slowly varying intensity is applied to a ferromagnetic material, an interaction occurs at the atomic level in small regions called domains; specifically, the walls of these domains are set in motion and when they come into contact with impediments to this motion such as dislocations, grain boundaries, precipitate particles, etc., a jump or pulse in magnetization occurs. These abrupt movements of the domain walls generate a crackling sound which may be sensed by appropriate acoustical equipment and is called Barkhausen noise. It is now known that Barkhausen noise may be correlated to material properties such as stress, grain size, grain form and orientation (hereinafter described as "texture"), and phase morphology. One such correlation technique is discussed in U.S. Pat. No. 3,427,872.

The present invention employs the known principles of Barkhausen noise to achieve a new, practical technique for the nondestructive testing of ferromagnetic steels to determine their anisotropic properties. For a better understanding of this invention, it is desirable to discuss anisotropy in greater detail.

Anisotropy

A material is said to be anisotropic if any of its properties, mechanical or microstructural, change as a function of direction. The properties may be hardness, certain magnetic properties, stress, texture, formability, strength, etc. If these properties are independent of direction, the material is said to be isotropic.

As suggested above, one form of anisotropy is called crystallographic texture. Metals consist of grains which have certain characteristic crystallographic orientations. If these orientations are random, the metal is isotropic. In contrast, metals consisting of grains with preferred crystallographic orientations are said to exhibit texture and are anisotropic. The presence of texture in a metal may be either advantageous or disadvantageous depending upon the application to which the metal is subjected. Also, certain types of textures may be more desirable than others.

Crystallographic texture in steels has a direct effect upon their mechanical properties because the strength of any crystalline material such as steel is different in different crystallographic directions. For example, the strength of the body centered cubic (bcc) structure of iron is strongest along the cube diagonal, or $<111>$ direction. It is less strong along the face diagonal, $<110>$, and weakest along the cube edge, $<100>$.

SUMMARY OF THE INVENTION

The present invention is directed to a nondestructive method for analyzing the anisotropic properties of ferromagnetic steels. The method involves the simultaneous, noncontact sensing of Barkhausen noise generated within a steel specimen in a plurality of directions. Accordingly, the present invention is ideal for the rapid evaluation of properties that are direction dependent and affords the steelmaker the opportunity to make process control corrections when undesirable properties caused by cold working and annealing, for example, are detected. The invention also provides the steelmaker with a higher degree of assurance than heretofore possible of the quality of a particular quantity of steel and its suitability for an intended purpose.

The present invention provides a method for analyzing the anisotropic properties of ferromagnetic steel comprising the steps of: generating Barkhausen noise within the microstructure of a sheet of the steel simultaneously in a plurality of directions; sensing the Barkhausen noise without physical contact between the sensing means and the sheet; and converting said Barkhausen noise as a function of direction within the sheet to usable intelligence with respect to anisotropic properties. The present invention affords the opportunity to continuously sense the Barkhausen noise and to do so while there is relative movement between the sensing means and the sheet.

In considering the present invention, it is important to realize that the intensity of Barkhausen noise is closely related to the distribution of easy directions of magnetization in the material, which in ferromagnetic steels are the crystallographic <001> directions. More specifically, the noise intensity follows the distribution of <100> directions, the higher the intensity of <100> directions, the higher the noise. The distribution of Barkhausen noise intensity in different directions on the specimen surface can thus yield information on the anisotropic properties of the material.

The present invention employs sensing means, described in detail hereinafter, that can detect Barkhausen noise components in all directions simultaneously. The method of the invention thus can generate information that directly describes the anisotropic characteristics of the test piece. The sensing means employed is capable of static contact measurements and dynamic, continuous non-contact measurements, the latter being essential for process control applications.

As will be shown hereinafter, it is necessary to measure Barkhausen noise intensities in at least a plurality of directions on the test piece surface at the same time using a multi-channel sensing means to obtain information useful for continuous process or quality control purposes. Examples will be given below on how the actual Barkhausen noise data relates to the anisotropic characteristics of steels.

Other details and advantages of the present invention will become apparent from the following detailed description taken with the accompanying drawings in which:

DETAILED DESCRIPTION OF THE PREFERRED EMBODIMENTS

The present invention will be described in detail below by reference to two practical examples where anisotropy plays a major role in the end use of steel. The first example is an undesirable surface condition called "roping" which affects the formability of the steel and which results from the presence of unfavorable crystallographic orientations developed during the working and/or annealing operations. The second example is an evaluation of magnetic properties, such as permeability or core loss, in transformer steels.

Formability and Roping

Formability is one of the important properties of sheet steel for most applications, e.g. press forming, deep drawing, stamping, etc. Formability is the capability of the steel to be extensively deformed into intricate shapes without fracture or the presence of defects in the finished part. The principal forms of deformation are drawing and stretching; drawing will be considered here in greater detail.

In drawing, it is desirable to maximize the ability of the material to flow in the plane of the sheet and to minimize the flow of material in a direction normal to the sheet. A measure of this condition, called plastic strain ratio (r), can be determined by the formula:

$$r = \frac{\epsilon_{width}}{\epsilon_{thickness}} \quad (1)$$

wherein $\epsilon$ = strain.

It is well known that r varies as a function of direction; see e.g. R. W. Vieth and R. L. Whiteley, "Influence of Crystallographic Orientation On Plastic Anisotropy In Deep Drawing Steel", "Anisotropy And Tensile Test Properties And Their Relationship To Sheet Metal Forming", IDDRG, London (1964). Since the properties in the plane of the sheet are usually different in different directions, the average strain ratios ($\bar{r}$) in the rolling direction (R.D.), transverse to the rolling direction (T.D.) and 45 degrees to the rolling direction may be used as a measure:

$$\bar{r} = \frac{r_{R.D.} + 2r_{45} + r_{T.D.}}{4} \quad (2)$$

An average strain ratio of 1 is indicative of equal flow strengths in the plane and thickness directions of the sheet. Further, the variation of the strain ratio in different directions in the plane of the sheet, $\Delta r$, is a measure of planar anisotropy according to the formula:

$$\Delta r = \frac{r_{R.D.} + r_{T.D.} - 2r_{45}}{2} \quad (3)$$

Thus, a completely isotropic material has strain ratio of 1 in each direction, i.e. $\bar{r}=1$ and $\Delta r=0$. An ideal deep drawing steel has both a high average strain ratio, $r>1$, and a $\Delta r$ of zero. It is also known that the higher the r, the deeper the draw.

It is well known that strain ratio is related to the crystallographic orientation of the grains in a sheet, that is, to the texture. It thus becomes useful to examine the relationship of crystallographic orientation and r to determine the most favorable textures for good formability. According to published sources, the theoretical values of strain ratio (r) in the rolling direction for four single crystal orientations are as follows:

| Texture | r |
| --- | --- |
| (001) [110] | $\simeq 0$ |
| (112) [1$\bar{1}$0] | $<1$ |
| (011) [01$\bar{1}$] | $\infty$ |
| (111) [01$\bar{1}$] | $>1$ |

These data confirm the favorable effect of a strong (111) texture and the unfavorable effect of the (001) texture. The (011) and (112) textures evidence high strain ratios in certain directions and may be even more favorable than the (111) texture, provided that the high r values are located in the rolling direction.

As stated above, an ideal deep drawing steel has both a high average strain ratio, $\bar{r}>1$, and a $\Delta r$ of zero. The (111) [01$\bar{1}$] texture fulfills these requirements best. Other textures, i.e. (112) and (011), may have high r values in some directions and may exhibit excellent deformation behavior in certain types of forming operations.

A particularly undesirable surface condition on ferritic stainless steels is the presence of corrugations aligned in the direction of rolling. This condition, known as roping or ridging, is known to be caused by the presence of certain textures. The most common textures in ferritic stainless steels are:

| (001) | [100] | cube on face | CF1 |
| --- | --- | --- | --- |
| (001) | [110] | cube on face | CF2 |
| (011) | [100] | cube on edge | CE1 |
| (011) | [0$\bar{1}$1] | cube on edge | CE2 |
| (111) | [0$\bar{1}$1] | cube on corner | CC1 |
| (111) | [11$\bar{2}$] | cube on corner | CC2 |

According to published sources, when the CF or CE texture is strong in a CC matrix and is distributed as clusters of grains or in bands, roping will develop during forming. Severe roping will occur when a well developed CF component is present in a material with a CC matrix, especially if the CF component is present in bands. Slight ridging will occur when a well developed CE component is present in a material with a CC matrix.

From the foregoing, it may be seen that on-line measurements of texture in ferritic stainless steels in accordance with the present invention can provide valuable information to the steelmaker with respect to the formability and surface characteristics of particular coils of finished steel. In making these measurements, the present invention employs the principle that the intensity of the Barkhausen noise varies with the distribution of crystallographic directions. On this basis, if texture is present, the intensity of the Barkhausen noise varies along different directions in the sheet plane and thus intensity patterns may be formed which in each case are representative of the texture present.

Figure 1:
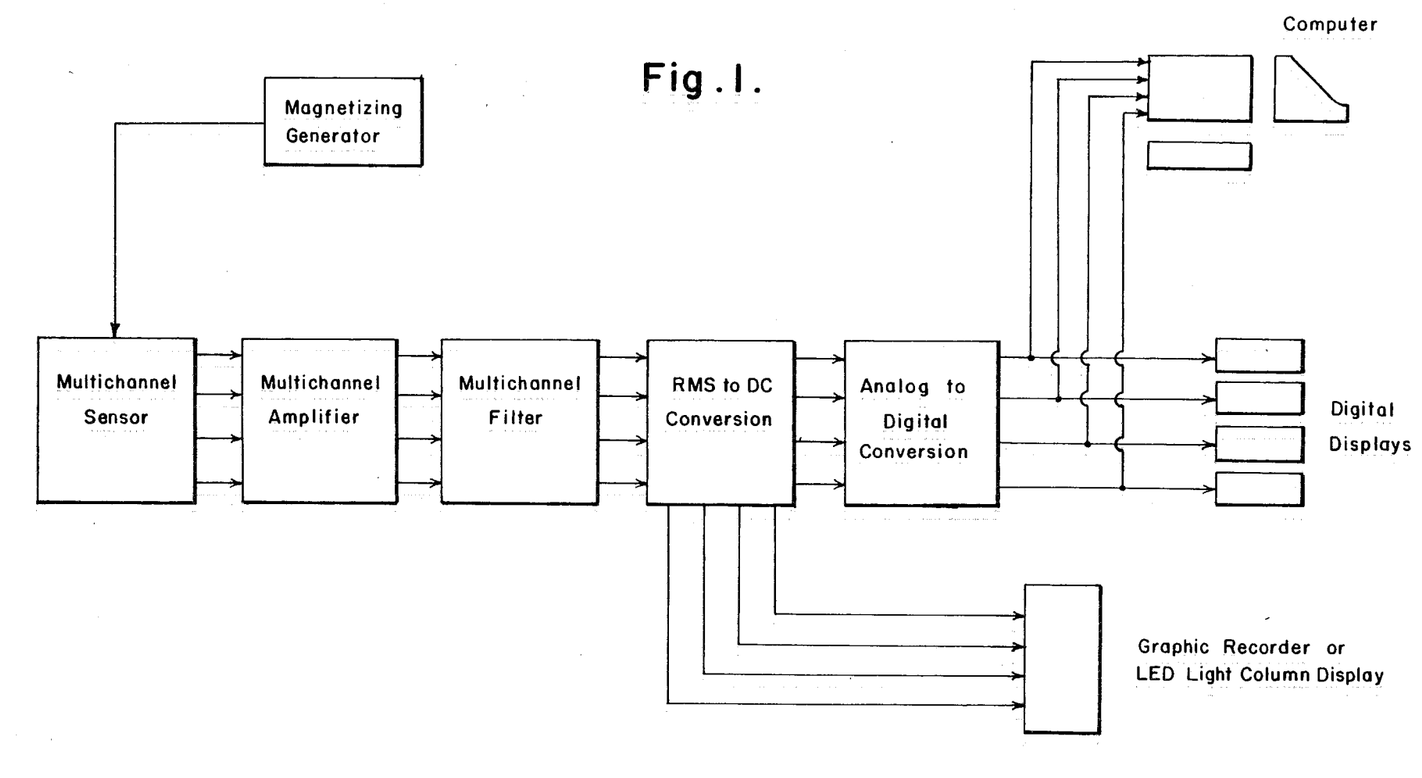
FIG. 1 is a schematic block diagram of a circuit for use in the present invention.

The present invention employs multi-channel, non-contact dynamic sensors of the type described in U.S. application Ser. No. 539,006, entitled SENSOR FOR GENERATING AND SENSING BARKHAUSEN NOISE, filed concurrently herewith and incorporated herein by reference, to detect Barkhausen noise in a direction parallel to each applied magnetizing field. As shown in FIG. 1, Barkhausen signals received from the multi-channel sensors are first amplified and then are filtered to obtain a proper signal level and frequency range for further analysis. The frequency range depends on the maximum speed of the steel specimen passing the sensors and the induced mechanical vibration to be eliminated. Amplified and filtered Barkhausen noise, which are AC signals, are then converted to DC signals proportional to the RMS level of the AC signals in every channel. The DC signals thus obtained can be input to a graphic chart recorder to provide a continuous plot of the signal levels. Alternatively, or in addition, the DC signals can be monitored in LED column displays that have adjustable upper and lower limit alarms. The DC signals so displayed and/or monitored are proportional to the intensity of Barkhausen noise in different directions on the specimen and can be related to the anisotropic characteristics of the specimen in a manner soon to be discussed.

A more sophisticated analysis can be made by converting the DC signals to digital by use of an analog-to-digital converter and displaying them in a numerical form or feeding the digital signals to a computer. The computer can be programmed to analyze and display the signals in a variety of well-known, useful forms, and to select good, satisfactory and poor material on a continuous basis and furnish corrective information to process control.

Figure 2:
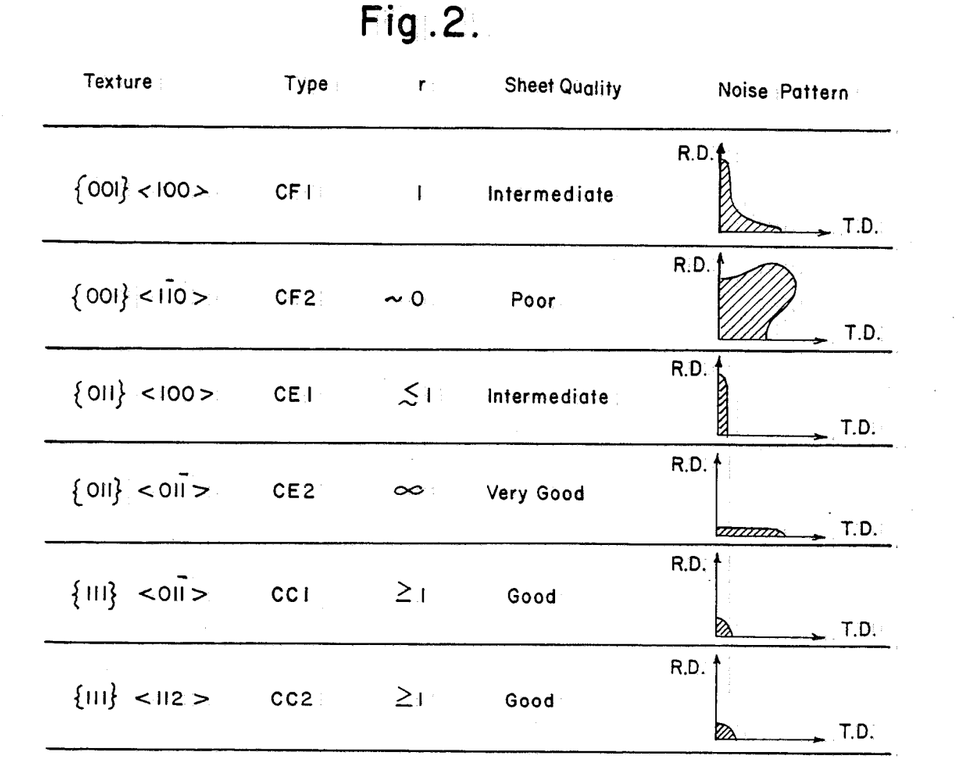
FIG. 2 is a tabulation, including representative Barkhausen noise patterns, of the texture components in the ferritic stainless steels.

Referring now to FIG. 2, there is shown the typical Barkhausen noise intensity patterns in the plane of the sheet for most common textures present in ferritic steels. These patterns are analyzed in the manner just described. The r values, in FIG. 2 are obtained from the Vieth and Whiteley source identified above and are those in the rolling direction. Further, the sheet quality identified in FIG. 2 is on the basis of r value in the rolling direction according to the relation:

| r | sheet quality |
| --- | --- |
| $\simeq 0$ | poor |
| $\simeq 1$ | intermediate |
| $>1$ | good |
| $\infty$ | very good |

It will be apparent to those skilled in the art that the Barkhausen noise intensity patterns preferably should depict pronounced characteristics in each case so that the textures present may be successfully distinguished from one another.

Figure 3:
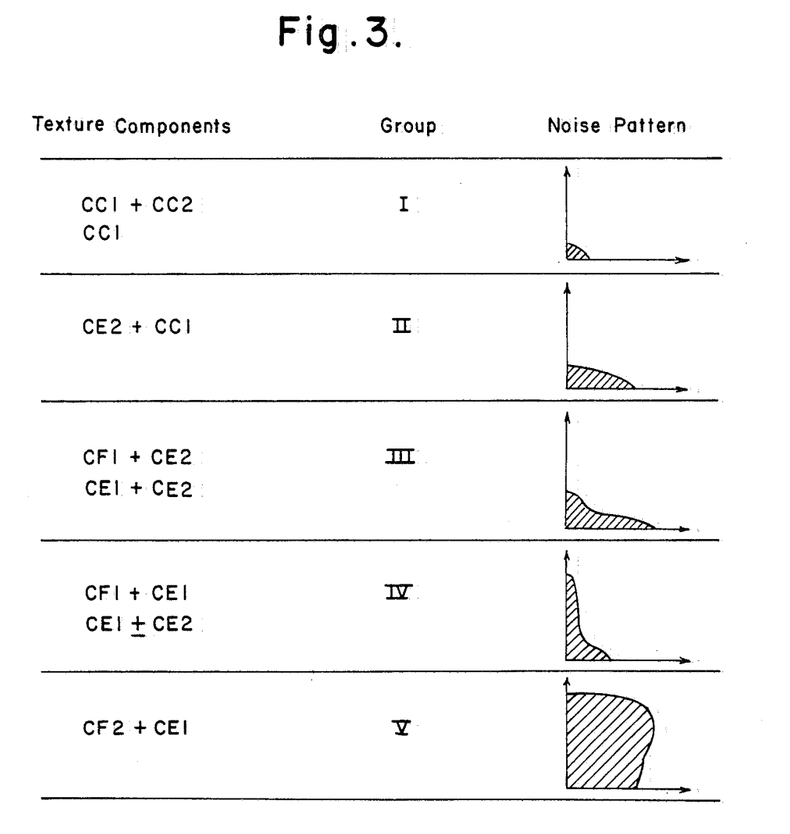
FIG. 3 illustrates the Barkhausen noise patterns and corresponding group classification for some combinations of the basic texture components displayed in FIG. 2.

In practice, a steel sheet often will exhibit several texture components instead of one. FIG. 3 illustrates some simple combinations of the basic texture components shown in FIG. 2; the Barkhausen noise intensity patterns for these combinations thus are a superimposition of the basic patterns. FIG. 3 gives examples of eight different combinations which may be further classified into Groups I to V having the characteristic noise intensity patterns shown. Table I below shows the relative sheet quality for Groups I to V. The quality associated with a particular texture in a combination is shown in parentheses in the first column and any strong texture component is underscored in that column.

TABLE I

Combinations of the basic texture components, group classification and the sheet quality.
The strong texture component is underlined.

| Texture components | Group | Sheet Quality |
|---|---|---|
| CC1(good) + CC2(good) | I | Good |
| CC1(good) | I | Good |
| CE2(very good) + CC1(good) | II | Good |
| CF1(intermediate) + CE2(very good) | III | Intermediate |
| CE1(intermediate) + CE2(very good) | III | Intermediate |
| CF1(intermediate) + CE1(intermediate) | IV | Intermediate |
| CE1(intermediate) + CE2(very good) | IV | Intermediate |
| CF2(poor) | V | Poor |
| CF2(poor) + CE1(intermediate) | V | Poor |

Table II below summarizes the experimental data for 39 different AISI 430 steel sheet samples.

TABLE II

Experimental results of magnetic noise measurements, group classification and rope rating.

| Sample No. | Magnetic Parameter 0° | 45° | 90° | 135° | Group | Roping Rating* |
|---|---|---|---|---|---|---|
| 1 | 3 | 4 | 5 | — | I | 0 |
| 2 | 39 | 55 | 143 | 51 | II | 0 |
| 3 | 96 | 102 | 157 | 97 | II | 0 |
| 4 | 115 | 137 | 160 | 122 | II | 0-1 |
| 5 | 62 | 70 | 142 | — | II | 0-1 |
| 6 | 65 | 82 | 105 | 78 | II | 1-2 |
| 7 | 74 | 88 | 127 | 93 | II | 4/5 mild |
| 8 | 165, 200 | 171, 200 | 193, 200 | 155, 200 | II + ? | 0-1 |
| 9 | 200 | 200 | 200 | 200 | ? | 1 |
| 10 | 105, 112 | 105, 106 | 125, 137 | 111, 97 | II + III | 0-1 |
| 11 | 17, 25 | 18, 19 | 42, 27 | 18, 18 | II + III | 1 |
| 12 | 102, 124 | 106, 108 | 160, 144 | —, 107 | II + III | 1 |
| 13 | 70 | 55 | 75 | 50 | III | 1 |
| 14 | 110 | 84 | 150 | 94 | III | 1 |
| 15 | 99 | 88 | 130 | 82 | III | 1-2 |
| 16 | 141 | 134 | 180 | 107 | III | 1-2 |
| 17 | 188, 175 | 145, 144 | 187, 163 | —, 147 | IV + CF1 | 0-1 |
| 18 | 87, 84 | 59, 55 | 65, 59 | —, — | IV | 0-1 |
| 19 | 82, 85 | 31, 39 | 71, 81 | —, — | IV | 1 |
| 20 | 48, 88 | 26, 32 | 48, 49 | —, — | IV + CF1 | 0 |
| 21 | 140 | 101 | 126 | 98 | IV | 3 |
| 22 | 105, 80 | 85, 76 | 93, 94 | 85, 71 | III + IV | 2-3 |
| 23 | 141, 185 | 124, 121 | 132, 117 | 117, 126 | IV + V | 1 |
| 24 | 188, 177 | 165, — | 157, 176 | 180, — | IV + V or III | 2 |
| 25 | 143, 138 | 106, 107 | 112, 96 | 100, 109 | IV + V | 3-4 |
| 26 | 190 | 164 | 107 | 160 | V | 2 |
| 27 | 170 | 147 | 100 | 141 | V | 4 |
| 28 | 200 | 150 | 70 | 145 | V | 1w |
| 29 | 200 | 185 | 70 | 200 | V | 3-4w |
| 30 | 140 | 110 | 105 | 110 | V | 3-4w |
| 31 | 185 | 153 | 145 | — | V | 4-5 |
| 32 | 169 | 141 | 114 | — | V | 4-5 |
| 33 | 142 | 121 | 99 | 109 | V | 4-5 |
| 34 | 200 | 194 | 106 | 200 | V | 4-5 |

TABLE II-continued

Experimental results of magnetic noise measurements, group classification and rope rating.

| Sample No. | Magnetic Parameter | | | | Group | Roping Rating* |
|---|---|---|---|---|---|---|
| | 0° | 45° | 90° | 135° | | |
| 35 | 121 | 74 | 61 | — | V | 4–5 |
| 36 | 115 | 73 | 53 | — | V | 4–5 |
| 37 | 188 | 124 | 99 | — | V | 4–5 |
| 38 | 200 | 144 | 100 | — | V | 4–5 |
| 39 | 189 | 133 | 119 | — | V | 5 |

Note:
*Determined visually after 10% elongation
w indicates weaving, a special surface condition
4/5 indicates a few deep corrugations The Barkhausen noise was measured in accordance with the present invention on an undeformed sample in the rolling direction and at 45, 90 and 135 degrees to the rolling direction. The magnetic parameter reported in Table II is an average of approximately 10 measurements on different locations on the sample surface. Occasionally two different types of noise intensity patterns were found for a single sample at different locations; in such cases, the values in Table II represent averages for each intensity pattern.

The data of Table II indicates that the 39 samples include all the Groups I to V as well as some combinations of Groups I to V. Table II also includes the digits 0 to 5 to describe the severity of the roping observed on the sample (5 being most severe). With a few exceptions, the roping rating increased with increasing Group numbers.

Figure 4:
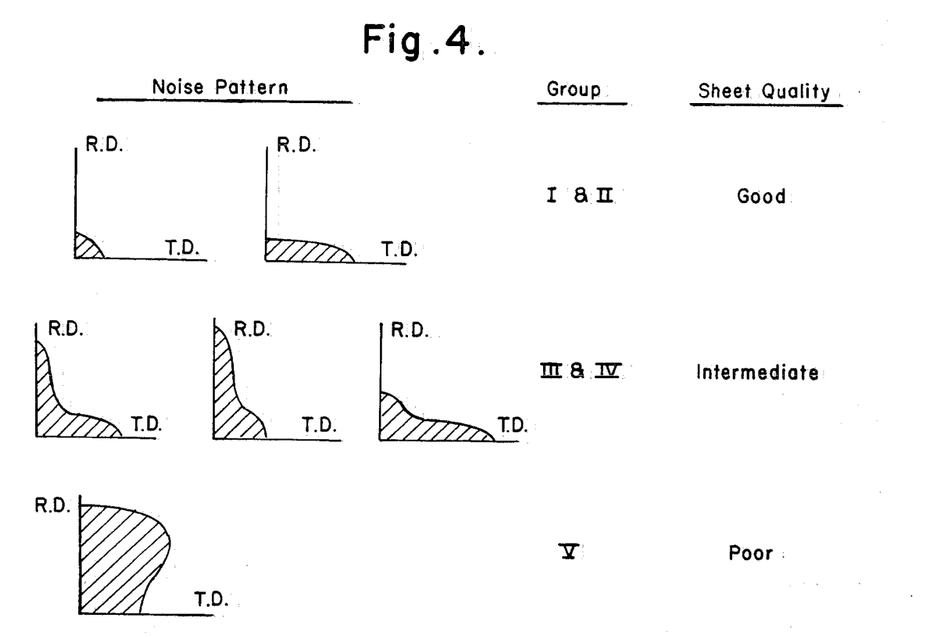
FIG. 4 illustrates, in summary form, the interrelationship between Barkhausen noise patterns, group classifications and sheet quality.

FIG. 4 gives a simplified description of the above results. If the Barkhausen noise intensity remains low in all directions from 0 to 90 degrees, or if it is low at 0 degrees and gradually increases towards 90 degrees, the intensity is described by groups I and II, and the sheet surface quality will be good after the forming operation. If the intensity will follow the patterns given in the second line of this Figure, the noise in described by groups III and IV, and the sheet quality will be intermediate. Finally, if the Barkhausen noise intensity at 90 degrees to the rolling direction is lower than that at 45 degrees, it belongs to group V, and the sheet quality will be poor.

The consistency in the results is excellent in the respect that the Group V steel sheets exhibiting poor surface quality can be separated with the present method from the steel sheets exhibiting good or intermediate surface quality with high confidence.

The present invention thus permits the steelmaker to separate Group V steel sheets, which exhibit poor surface quality, from steel sheets exhibiting good or intermediate surface quality with a high degree of confidence.

Magnetic Properties

In transformer steels, it is desirable to have the <001> easy directions of magnetization, i.e. the preferred crystallographic direction of the magnetization vector of magnetic domains oriented in a certain way. This orientation will result in optimum magnetic properties like higher permeability and lower core loss, which properties are important for commercial use of such materials. The most common desirable texture type is designated (110) [001]. In this type of texture, the <001> easy directions of magnetization are on an average parallel to the sheet surface and parallel to each other between different grains of the sheet. The sharper this kind of grain orientation, the better the magnetic properties. Efficient rolling and annealing processes to produce this kind of grain orientation have been known for decades.

The present invention can be advantageously applied to the evaluation of grain orientation in transformer steels. For such evaluation, only a two channel, noncontact dynamic sensor of the type disclosed in the aforementioned U.S. patent application Ser. No. 539,006, filed concurrently herewith, is needed because, as explained hereinbelow, measurements of the Barkhausen noise intensity in only the rolling direction and transverse to the rolling direction are required to determine the intensity of the preferred texture.

Figure 5:
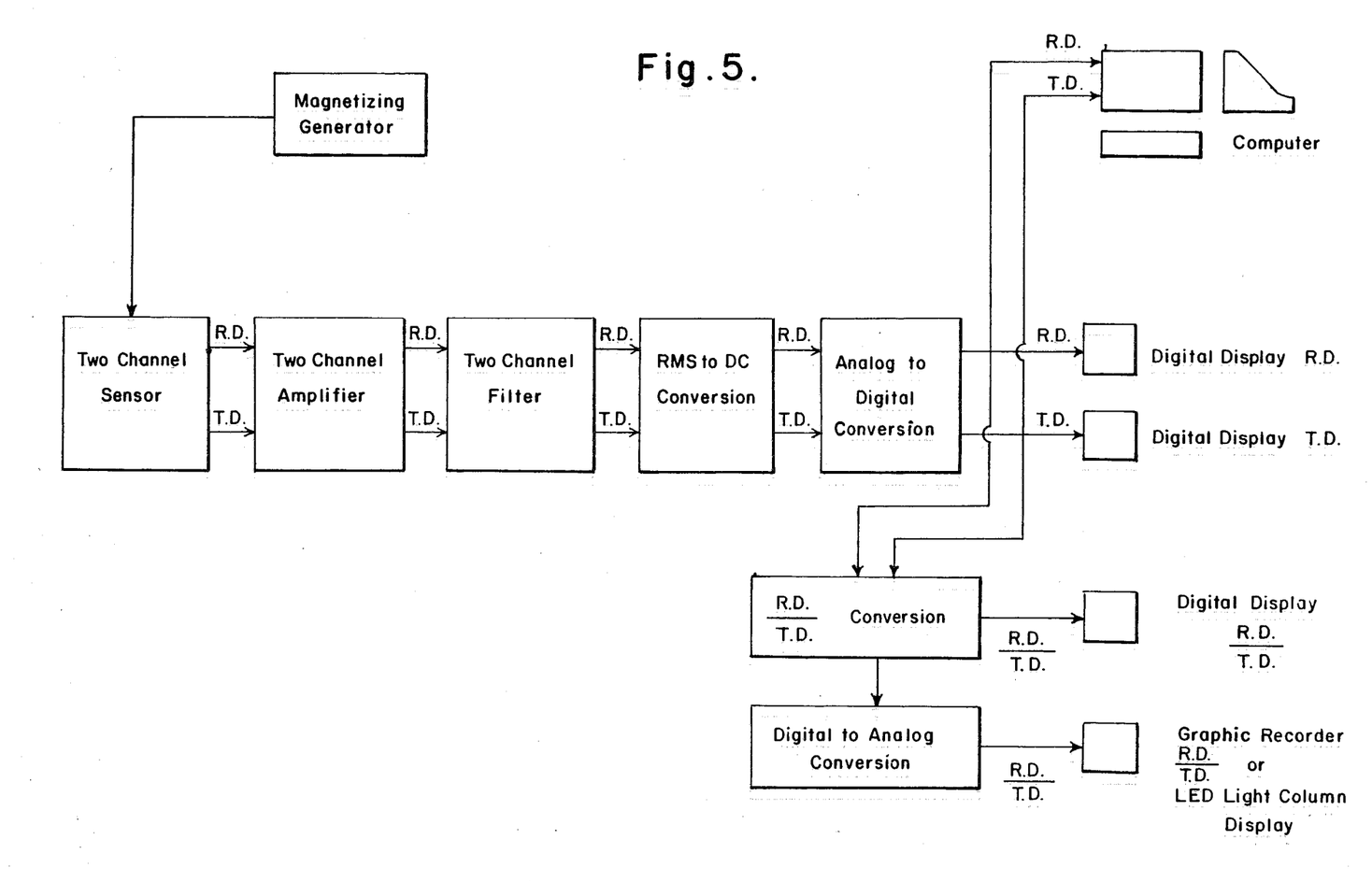
FIG. 5 is a schematic block diagram of an alternate circuit for use in the present invention.

As may be seen in FIG. 5, Barkhausen signals received from the two-channel sensor are processed in the same manner as that described in connection with FIG. 1 above. The DC signals are converted to digital and are processed by computer as described above; alternatively, or in addition, the digital signals may be displayed in numerical form or processed as a ratio R.D./T.D. next to be described. As in the earlier discussion, information obtained on-line by the process of the present invention may be transmitted to control or to aid in the control of the manufacturing process.

As referred to above, it is desirable in grain-oriented silicon steels that the (110) plane be parallel to the strip surface and the [001] direction be parallel to the rolling direction. The higher the intensity of this texture, the greater the permeability and the lower the core loss.

Figure 6:
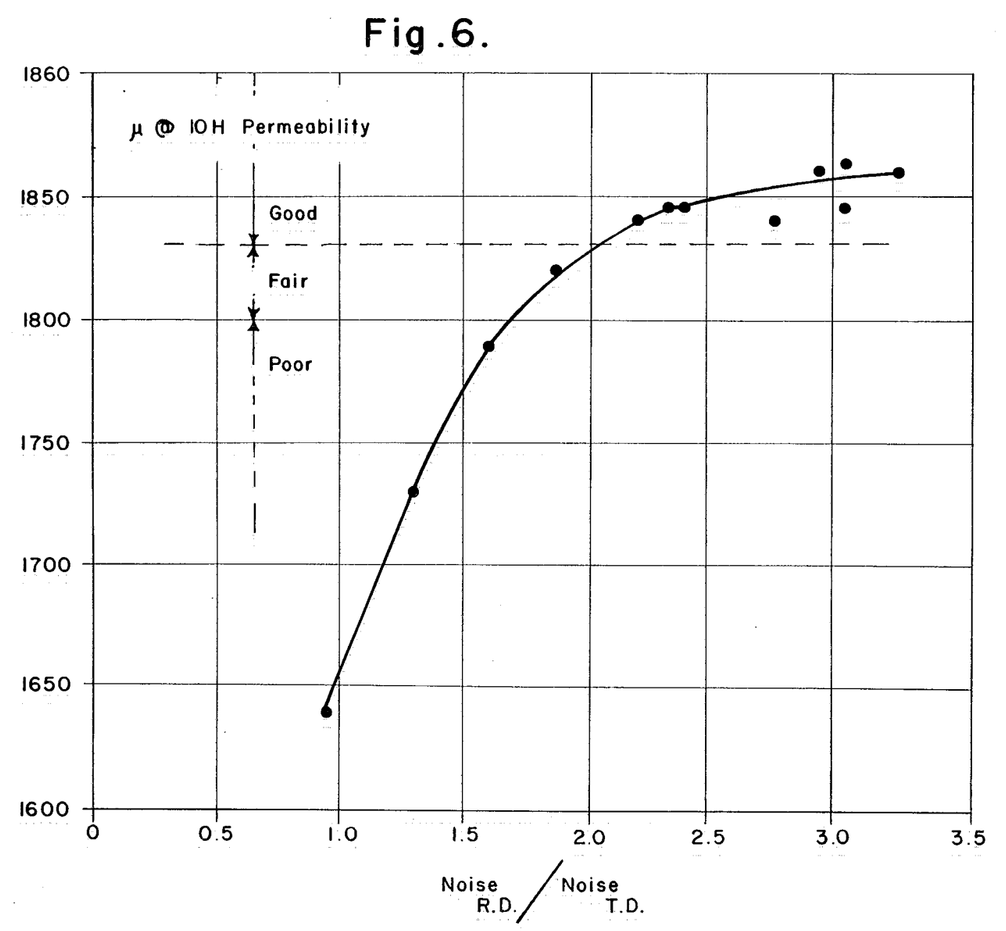
FIG. 6 is a plot of the relationship between permeability (expressed in $\mu$ @ 10H) vs. magnetic noise ratio ($noise_{R.D.}$/noise $_{T.D.}$).

As shown in FIG. 2, the (110) [001] texture yields a high intensity Barkhausen noise in the rolling direction and a low intensity noise in the transverse direction, i.e., a high value of the (noise intensity$_{R.D.}$/noise intensity$_{T.D.}$) ratio. Thus, relatively high values of this ratio are indicative of the presence and intensity of (110) [001] texture in grain-oriented silicon steels. FIG. 6 is a plot of the aforementioned noise intensity ratio against permeability for twelve difference sheets of steel. It may be seen that if the noise intensity ratio is greater than approximately 2, the corresponding permeability is greater than 1830, a value which may be considered good permeability. If the ratio is less than approximately 1.7, the corresponding permeability will be less than 1800, a value which is considered poor permeability. Noise intensity ratios between 1.7 and 2 yield permeabilities in the range between 1800 and 1830, which range is considered to be indicative of fair permeability.

What is claimed is:

1. A method for determining the suitability of rolled ferromagnetic steel for further forming operations comprising the steps of:

generating Barkhausen noise within the microstructure of said steel simultaneously in at least three different directions;

sensing said Barkhausen noise in each of said directions without physical contact between the means for sensing and said steel;

continuously monitoring the intensity variation of said sensed Barkhausen noise in each of said directions;

constructing a noise pattern based on the Barkhausen noise intensity variations sensed in all of said directions; and comparing said pattern against predetermined Barkhausen noise intensity patterns representative of various steel qualities.

2. A method as recited in claim 1 wherein: there is relative movement between said sensing means and said sheet of steel.

3. A method as recited in claim 2 wherein: said generating and sensing steps are conducted continuously.

* * * * *